US009241861B2

(12) United States Patent
Bissell et al.

(10) Patent No.: US 9,241,861 B2
(45) Date of Patent: Jan. 26, 2016

(54) PORTABLE SPINAL DECOMPRESSION DEVICE

(71) Applicants: Charles Richard Bissell, Santa Barbara, CA (US); Gregory Brian Perkins, Santa Barbara, CA (US); John Stump, Santa Barbara, CA (US)

(72) Inventors: Charles Richard Bissell, Santa Barbara, CA (US); Gregory Brian Perkins, Santa Barbara, CA (US); John Stump, Santa Barbara, CA (US)

( * ) Notice: Subject to any disclaimer, the term of this patent is extended or adjusted under 35 U.S.C. 154(b) by 316 days.

(21) Appl. No.: 13/782,875

(22) Filed: Mar. 1, 2013

(65) Prior Publication Data

US 2014/0249461 A1 Sep. 4, 2014

(51) Int. Cl.
*A61F 5/00* (2006.01)
*A61H 1/02* (2006.01)

(52) U.S. Cl.
CPC ............ *A61H 1/0218* (2013.01); *A61H 1/0292* (2013.01); *A61H 2201/018* (2013.01); *A61H 2201/0161* (2013.01); *A61H 2201/0173* (2013.01); *A61H 2201/1215* (2013.01); *A61H 2201/1607* (2013.01); *A61H 2201/1664* (2013.01); *A61H 2203/0456* (2013.01)

(58) Field of Classification Search
CPC ............ Y10T 29/49826; Y10T 16/547; Y10T 29/49002; Y10T 156/1039; Y10T 156/1062; Y10T 16/52; Y10T 16/5321; Y10T 16/53225; Y10T 16/540255; Y10T 16/540257; Y10T 16/61; Y10T 24/3705; Y10T 29/02; A24C 5/35; A61G 13/101; A61G 13/12; A61G 13/122; A61G 13/123; A61G 2200/32; A61G 7/1015; A61G 7/1044; A61G 7/1055; A61G 57/14; B65G 57/14; B65G 2201/0226; B65G 47/5154
USPC ................................................ 602/32, 36, 34
See application file for complete search history.

(56) References Cited

U.S. PATENT DOCUMENTS

| | | | | |
|---|---|---|---|---|
| 1,314,002 | A | 8/1919 | Lee | |
| 3,405,931 | A * | 10/1968 | Anderson | 5/612 |
| 4,220,147 | A | 9/1980 | Allen | |
| 4,356,816 | A | 11/1982 | Granberg | |
| 4,534,341 | A * | 8/1985 | Bart et al. | 606/241 |
| 5,052,378 | A | 10/1991 | Chitwood | |
| 5,451,202 | A * | 9/1995 | Miller et al. | 602/36 |
| 6,939,269 | B2 | 9/2005 | Makofsky | |
| 7,033,333 | B1 * | 4/2006 | Croft et al. | 602/36 |
| 7,048,700 | B1 | 5/2006 | Gustie | |
| 2009/0299248 | A1 | 12/2009 | Cha | |
| 2010/0292051 | A1 | 11/2010 | Benumof | |

* cited by examiner

*Primary Examiner* — Michael Brown

(57) ABSTRACT

The present invention is a portable device for administering spinal decompression therapy. The device features a compact size and an innovative tension control mechanism to facilitate, in particular, a therapy for imbibition. The use of fabric for a sling and a platform adds comfort features while reducing weight.

13 Claims, 7 Drawing Sheets

PORTABLE SPINAL DECOMPRESSION DEVICE

This is a Non-Provisional Patent Application.

FIELD OF THE INVENTION

This invention relates to medical traction devices, and particularly to portable spinal decompression mechanisms.

BACKGROUND OF THE INVENTION

Traction devices for stretching the neck and spine are commonly used in hospitals, physical therapy clinics and other therapeutic venues. Typically, such devices apply a measured amount of force directed to decompress the spine and give relief from back pain caused by injury or degenerative effects. Specifically, they are used to treat disc bulges, disc herniations, facet syndrome, nerve impingement, spinal/foraminal stenosis, degenerative disc disease, osteoarthritis in the spine, muscle spasm, tension headaches, decreased joint space, decreased range of motion and facet joint inflammation. Typically, the apparatus includes some type of sling or harness to cradle the head with pressure applied thereto by means of pulleys and weights, often involving fixtures to a bed or wall. Commonly, assistance from another is needed to setup the gear and monitor its use.

In the technology of non-surgical spinal decompression, one therapy of particular utility is that of Imbibition. Imbitition involves the gentle stretching and relaxing of the spine to foster hydration and blood flow to the spinal discs. Such action applied along the cervical spine can create a negative pressure in the center of the intervertebral disc. The negative pressure fosters a suctioning effect, or vacuum phenomenon, which reduces the size of a herniated or bulging disc's gelatinous internal nucleus pulposus. The technique diminishes, or eliminates, nerve compression, while an osmotic gradient is created thereby helping to bring nutrients and water into the disc. The intervertebral discs have poor circulation and depend upon receiving nutrition by diffusion across the end plates of vertebrae above and below.

The "pumping action" created by the stretching and relaxing occurs naturally in the healthy case with daily motions and body positions. In the damaged or degenerative case, however, this gratuitous pumping action may be reduced or lost with disastrous effect to the already-poor circulation. A non-invasive remedial therapy, therefore, is to re-supply the disks with nutrients and blood that help the disks heal from inside out. This type of therapy is preferably practiced on a daily basis; and, therefore, as a matter of practicality, must be free from an institutional setting. Hence, the need arises for portable traction devices that are readily at hand for unassisted use.

Portable traction devices are described in U.S. Pat. No. 5,052,378 to Chitwood and U.S. Pat. No. 4,356,816 to Granberg. In both cases, a bed or platform supports a prone patient over a box frame housing a take-up apparatus. The take-up apparatus selectively applies tension to a head harness through an attached boom structure. The large frame members, such as the box, however, do not lend themselves to a compact configuration for storage or travel. It would be hard to imagine the Chitwood or Granberg device used in a hotel room on a trip, for example.

U.S. Pat. No. 5,451,202 to Miller discloses an apparatus without the bed which can be disassembled for storage. The storage configuration, nevertheless, made unwieldy by one out-sized frame member, is anything but compact. In addition, Miller teaches an overhead control requiring the patient to lift one or more arms to reach and operate the control. The lifting of an arm, and particularly the upper arm, from its prone position at rest activates the back musculature. Tension in the back muscles is not conducive to the relaxing effect sought in Imbibition Therapy. Further, Miller applies tension through a ratchet mechanism that cannot be incrementally backed off without tripping a release and jarringly withdrawing tension. Preferably, in the case of Imbibition, the tightening and slackening are smoothly applied in incremental measure and without the patient feeling abruptness or discontinuity.

There is an unfulfilled need in the state-of-art for an easy-to-assemble traction device which can be reduced to a compact and travel-friendly profile, and which can be operated to apply tension optimally to the spine for Imbibition Therapy and for pain relief.

SUMMARY OF THE INVENTION

The present invention addresses the shortcomings and gaps in the current art field with novel solutions and improvements. It is, therefore, an object of the present invention to provide a fraction device for personal use which is easy to assemble, lightweight and collapses into compact form. It is a further object to make the head-halter component comfortable for the patient's head through shaping, material selection and adjustment parameters. It is a further object to provide a tensioning control which is incrementally adjustable in both tightening and slackening and which indexes positions smoothly. It is a further object to use a worm gear for reversible action and position hold. It is a further object to operate the tensioning device while maintaining complete relaxation of the back muscles. It is a further object to provide leverage through gear ratios to make operation of the tensioning control as convenient and effortless as possible. It is a further object to provide an emergency relief button to instantly release traction. It is a further object to provide an automatic force limiter as a safety feature.

These objects, and others to become hereinafter apparent, are embodied in a portable device for spinal decompression therapy comprising, in a first part, a support base with two hingeably-attached horizontal members deployed a shoulder-width apart. In another part, a fabric web is stretched between the horizontal members for deployment at least partially beneath the back of a person lying against the fabric web, the body-weighed fabric web anchoring the support base to a level surface. In another part, a vertical structure is hingeably attached to the support base and deployed there upon at a first preferred vertical angle to fixedly position a distal end overhead. In another part, a hammock is suspended from the distal end to cradle the person's head at a second preferred vertical angle. In a last part, a means is provided for incrementally applying and releasing tension to the hammock, the manipulation of tension alternately stretching and relaxing the person's cervical spine along the second preferred vertical angle, the means including an automatic release of tension when a preferred critical value is reached. The portable device so configured may be folded and rolled up into a compact profile.

In a preferred embodiment, the means for incrementally applying and releasing tension comprises a reversing worm gear actuated by rotating a handle, the worm gear locking progress at each advanced position of the handle. A gear chain is enmeshed with the worm gear, the gearing apparatus designed to achieve mechanical leverage for comfortable hand operation. The gear chain drives a drum which spools an inner steel wire of a Bowden cable, the inner steel wire connected at a distal end thereof to the hammock.

As this is not intended to be an exhaustive recitation, other embodiments may be learned from practicing the invention or may otherwise become apparent to those skilled in the art.

DESCRIPTION OF THE DRAWINGS

Various other objects, features and attendant advantages of the present invention will become fully appreciated as the same becomes better understood through the accompanying drawings and the following detailed description, in which like reference characters designate the same or similar parts throughout the several views, and wherein.

DETAILED DESCRIPTION OF THE PREFERRED EMBODIMENT

Unless the context clearly requires otherwise, throughout the description and the claims, the term "tension" will be taken to refer to the tension force communicated by the Bowden cable, or equivalent, to the patient; the term "bias" will be taken to refer to the compressive reaction of the spring, or equivalent; and the complex term "gear train" will be taken to refer to the inter-meshed gears between and including the worm-gear follower and the driving gear of the drum, or equivalents.

Figure 1:
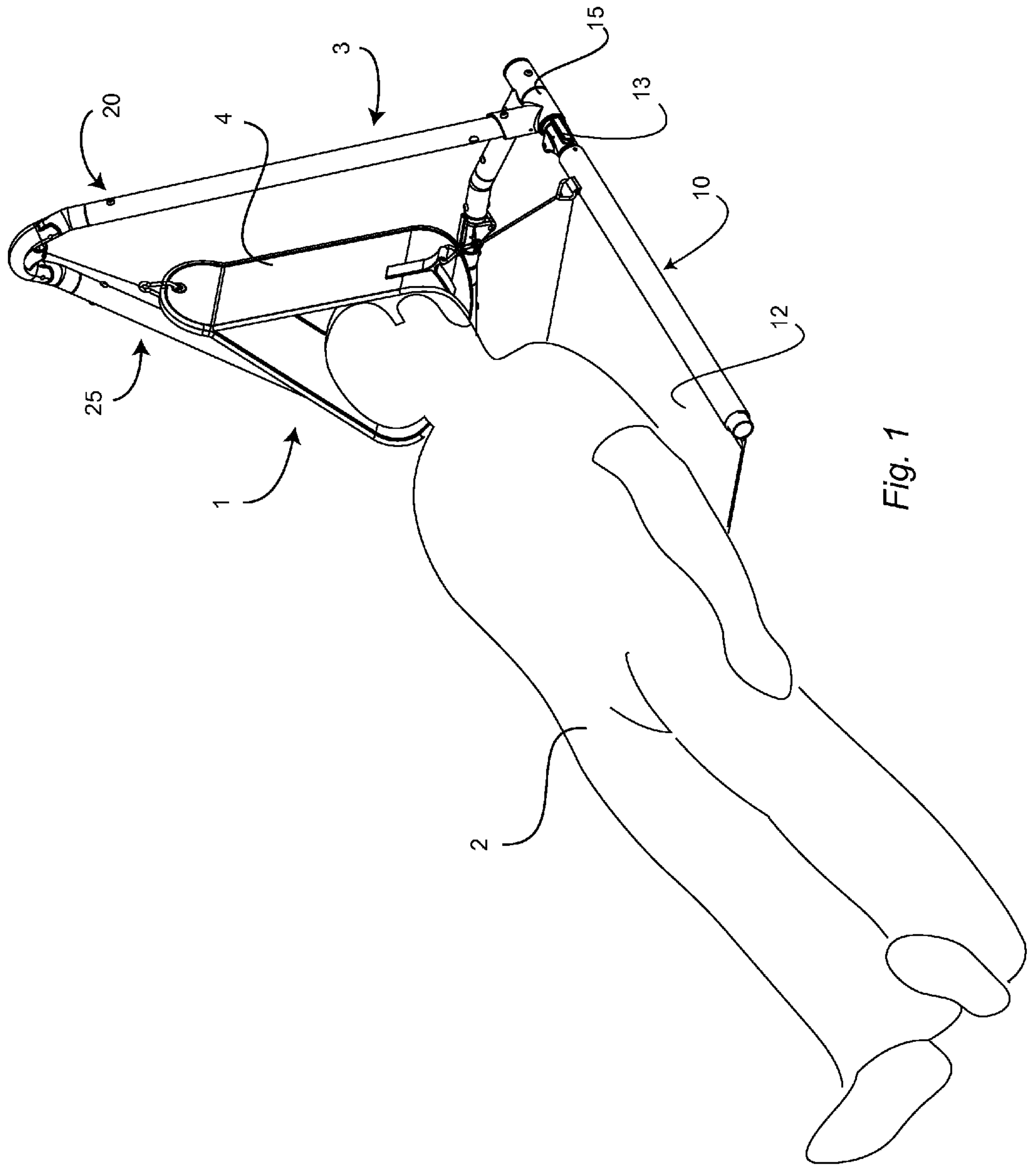
FIG. 1 is perspective view of the portable decompression device with a patient in position for its operation.
Figure 2:
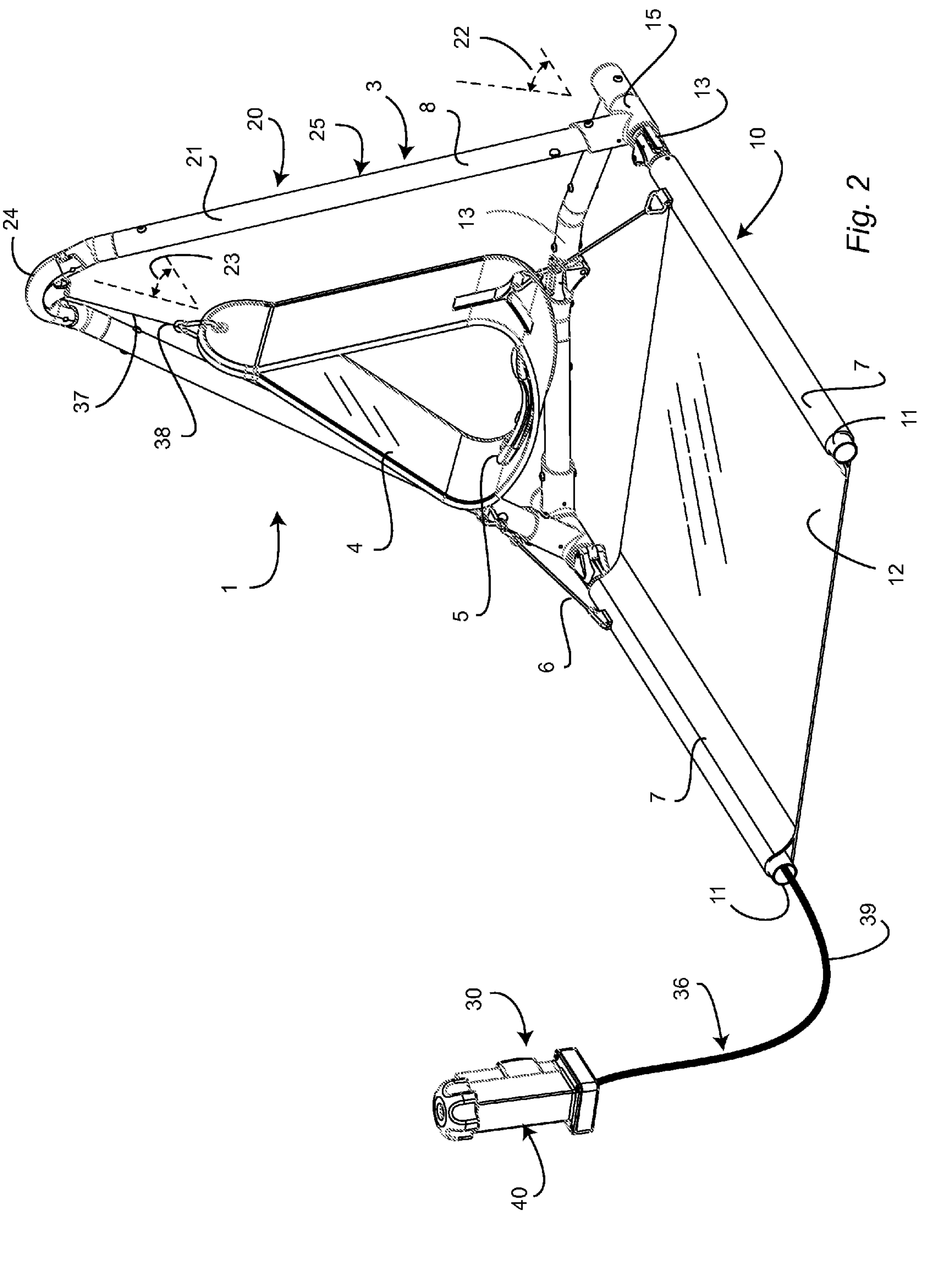
FIG. 2 is a perspective view of the portable decompression device.
Figure 3:
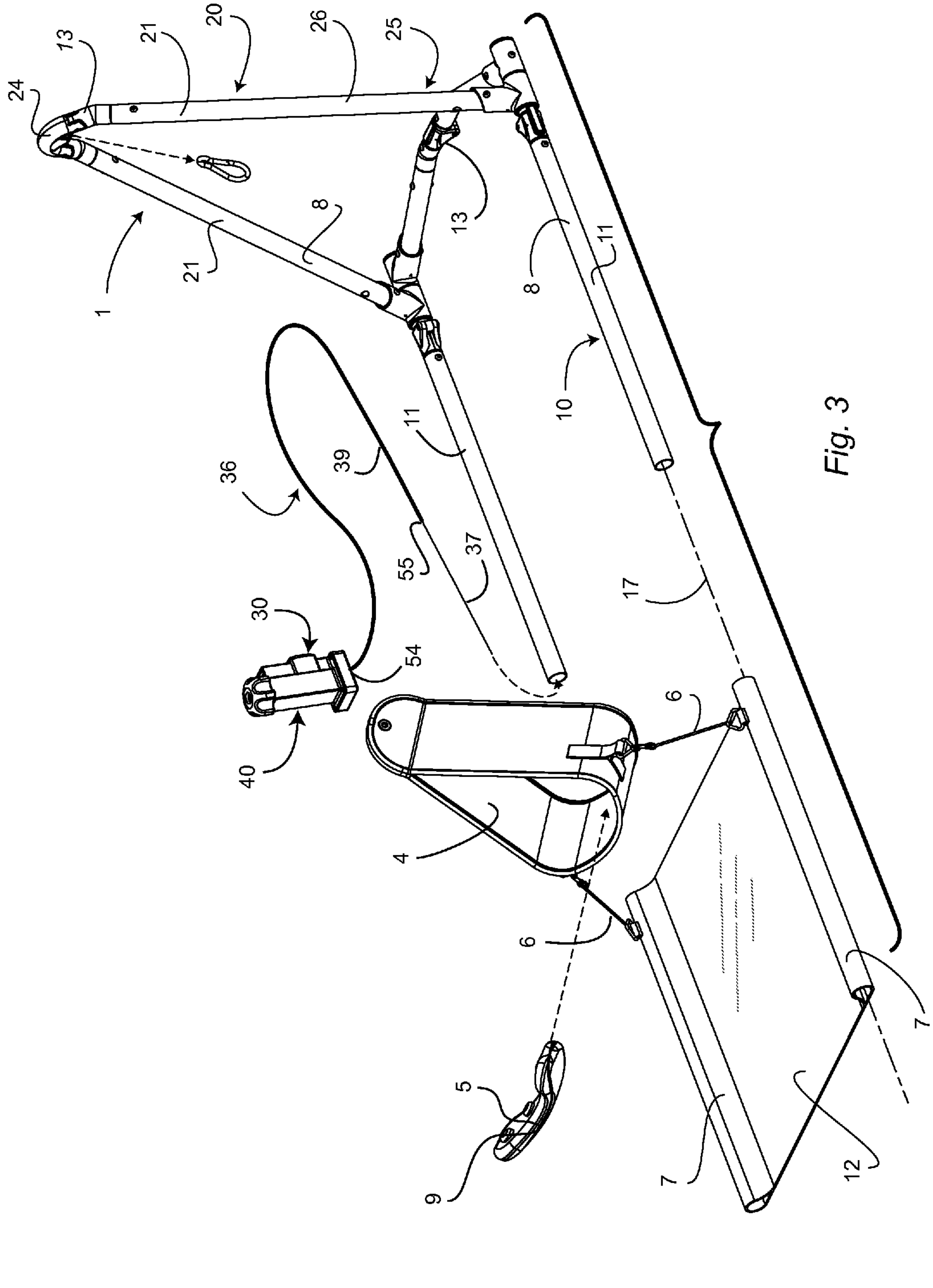
FIG. 3 is an exploded view of the portable decompression device.
Figure 5:
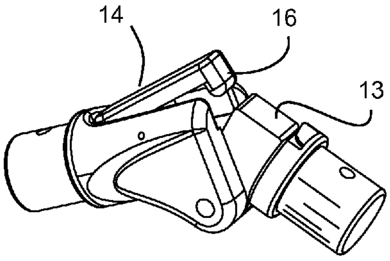
FIG. 5 is a detail view of an articulated hinge showing the toggle locking mechanism.

FIGS. 1-3 show the constituent elements of a portable decompression device 1. A frame 3 supports a hammock 4 to suspend the head of a patient's body 2 during use of the apparatus. The hammock 4 is manipulated by a means for applying and reversing tension 30. The frame 3 is comprised of a support base 10 and a vertical structure 20. The vertical structure 20 is attached through at least one hingeable joint 13 to the support base 10. The support base 10 is comprised of two horizontal members 11, which are connected by another iteration of the hingeable joint 13. When the support base 10 is deployed, the two horizontal members are spaced a shoulder-width apart, referencing the patient's body 2. A fabric web 12 spans between the two horizontal members 11 with sleeves 7 on opposing ends thereof jacketing, or otherwise attaching to, each horizontal member 11.

The fabric web 12 serves as a mat beneath the upper torso of the patient body 2 while the patient lies face-up on a level surface 7 (not shown), such as a floor. The fabric web 12 anchors the support base 10, and, therefore, the structurally-connected fame 3, to the level surface 7. The anchor is sufficient to immobilize the frame 3 when tension is applied to the patient's body 2.

The vertical support 20 may be a tower 26 in one embodiment. In the preferred embodiment, the vertical support 20 is comprised of an A-frame 25. The A-frame 25 is comprised of two struts 21. The two struts 21 are connected together at the distal end 24 of the vertical support 20 by at least one iteration of the hingeable joint 13. The two struts 21 are rotatably connected to the support base 10, each strut 21 to a corresponding horizontal member 11, through T-joints 15. T-joints 15 fix the inclination of the A-frame 25 relative to the level surface 7 according to a first preferred vertical angle 22 (FIG. 2). The first preferred vertical angle 22 sways the structure backwardly and serves to vector the applied tension both horizontally and vertically in a way optimized for the cranial and spinal curvatures. In the preferred embodiment, the first preferred vertical angle 22 is between 60° and 75°. In a particular preferred embodiment, the first preferred vertical angle 22 is nominally 68°.

Figure 4:
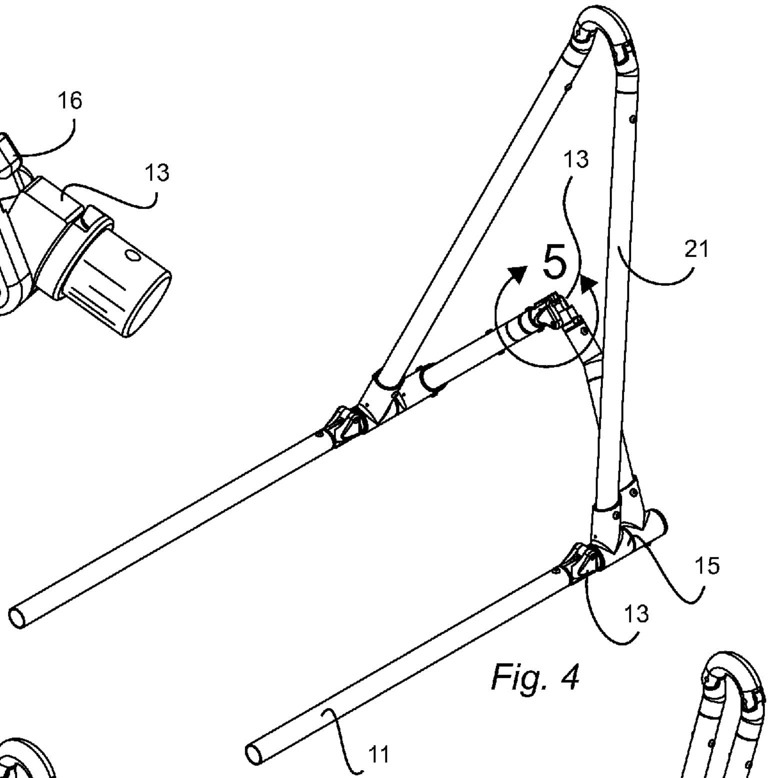
FIG. 4 is a perspective view of the frame elements of the device with the support component partially folded.
Figure 7:
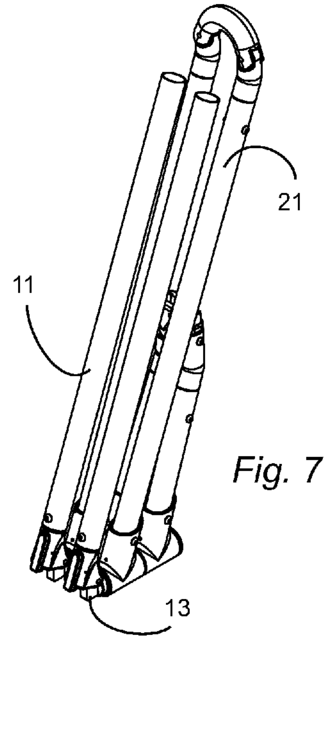
FIG. 7 is a perspective view of the fully folded frame.
Figure 6:
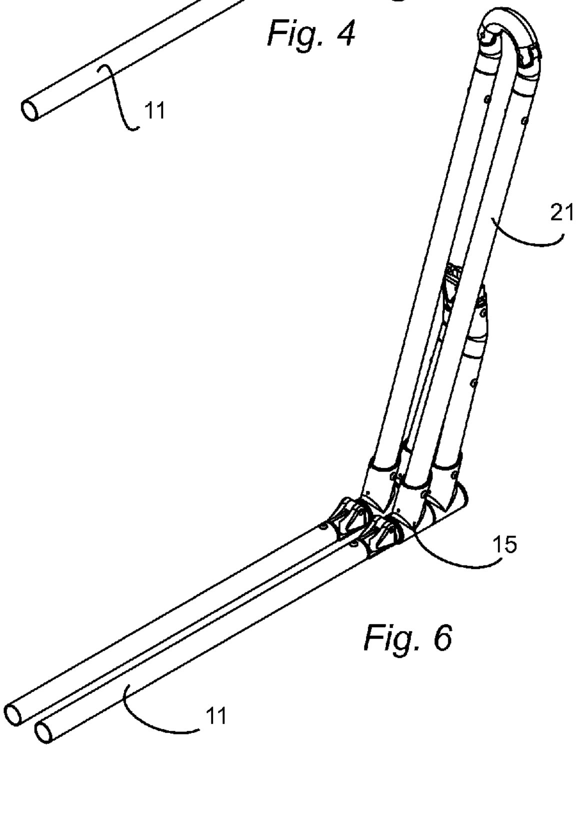
FIG. 6 is a perspective view of the frame elements showing the support component fully folded.
Figure 8:
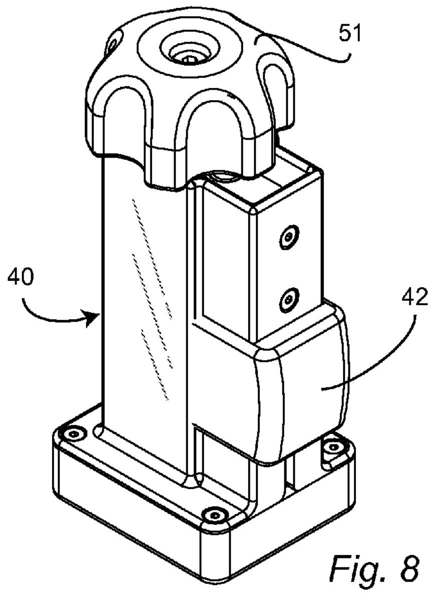
FIG. 8 is a perspective view of the traction control mechanism.

The frame 3 is collapsible, as shown in FIGS. 4-7. The hingeable joint 13 is immobilized in its extended position by toggle lock 14. Toggle lock 14 is comprised of a pawl 16, which can be toggled by hingeable connection to one part of hingeable joint 13 into and out of a corresponding recess (not shown) in the connecting part of hingeable joint 13. T-joint 15 is rotatable about a longitudinal axis 17 (FIG. 3) located at each horizontal member 11. With the articulation of joints here above described, the frame 3 may be folded into a compact configuration, as shown progressively in FIGS. 4-7. FIG. 4 shows the horizontal fold beginning, which is then completed in FIG. 6 and joined by the vertical fold in FIG. 7. When the frame 3 is unfolded and locked in its deployment arrangement, the structure is rendered rigid.

Figure 16:
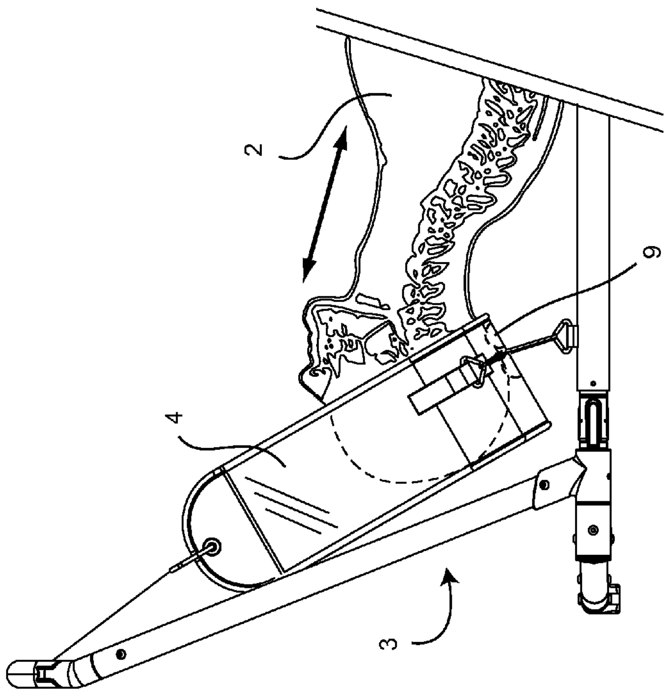
FIG. 16 is a partial elevation view showing the skeletal sine after stretching.
Figure 17:
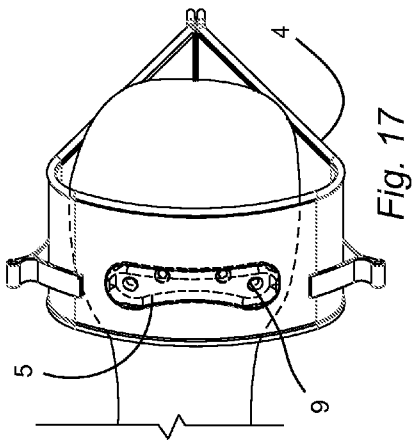
FIG. 17 is a plan view of the contoured occiput collar showing the fingers.
Figure 15:
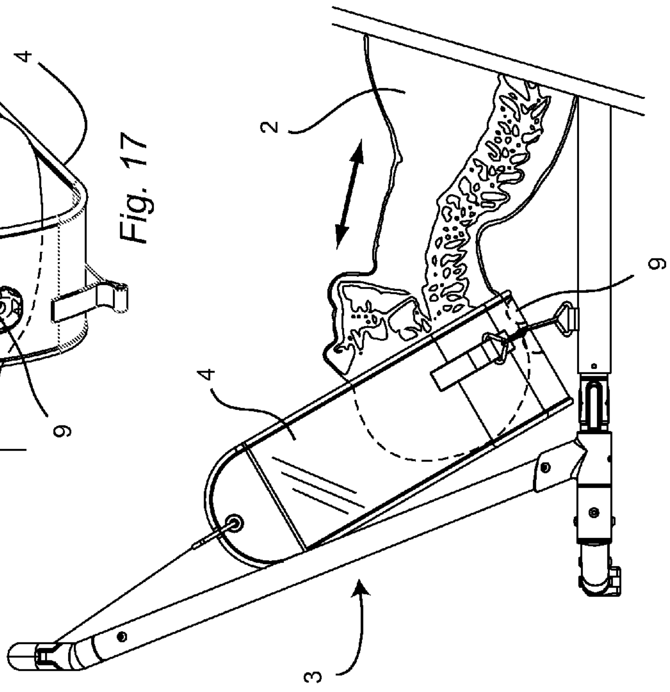
FIG. 15 is a partial elevation view showing the skeletal spine before stretching.

The hammock 4 is suspended from the distal end 24 of the vertical structure 20 at a second preferred vertical angle 23 (FIG. 2). The second preferred angle 23 is designed to allow the head to comfortably tilt back from the neck to position the occiput (back of the head) advantageously for the hammock 4 to grip thereupon and stretch the cervical spine. FIGS. 15 and 16 illustrate this stretching action with a skeleton cartoon. In FIG. 16, the vertebrae of the neck are shown in exaggerated extension. While the second preferred angle 23 may be initially set by elastically guying it with stabilizer lines 6 from strategically-placed anchor points on the support base 10, it may be adjusted for comfort by the patient shifting forward or rearward over the support base 10. In the preferred embodiment, a spongy occiput collar 5 is used to comfortably cradle the head (FIGS. 3 and 15-17). The occiput collar 5 has proud fingers 9 to gently grip the head as it partially wraps around the back of the head at the cranial base. In the preferred embodiment, the second preferred vertical angle 23 is between 55° and 65°. In a particular preferred embodiment, the second preferred vertical angle 23 is nominally 60°.

The hammock 4 is suspended from the distal end 24 of the vertical structure 20 by the means for applying and reversing tension 30. The means for applying and reversing tension 30 is comprised of a Bowden cable 36. Bowden cables are familiar from bicycle technology, where they are used in the actuation of brakes and gears. The Bowden cable 36 is comprised of an outer sheath 39, which is essentially a flexible conduit fixing a pre-determined running distance between an operating end 54 and a running end 55, combined with an inner steel wire 37 channeled there within.

Figure 12:
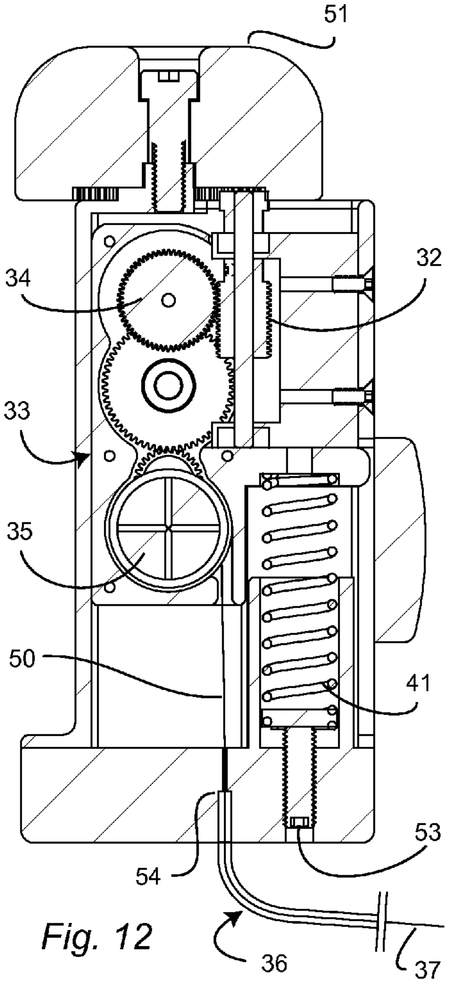
FIG. 12 is a section view taken along lines 12-12 of FIG. 11.
Figure 9:
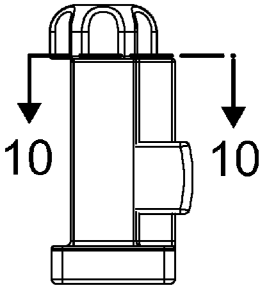
FIG. 9 is an elevation view of the traction control mechanism.

The spans of frame 3 between joints are bridged with tubular members 8. Tubular members 8 are fastened to hingeable joints 13 and T-joints 15 by rivets, or by other fastening means known in the art. Select hollow tubular members 8, combined with apertures through the intermediary joints, provide a passage for the Bowden cable 36 to be threaded from an open end of one of the horizontal members 11 to and through the distal end 24 of the vertical structure 20. The inner steel wire 37 exits the passage and the outer sheath 39 to connect at its distal end 38 with the hammock 4 and convey thereto a tension force which may be applied remotely at its proximal end 50 (FIG. 12). A turning block, or sheave, may be used at the exit point (not shown) to reduce friction.

The means for applying and reversing tension 30 further comprises a tension control mechanism 40, as best shown in FIGS. 8-14. The tension control mechanism 40 is located at the operating end 54 of the Bowden cable 36, where the pre-determined running distance of the cable positions it anywhere within reach of the patient; and, particularly, where the patient may access it with minimal arm movement. The tension control mechanism 40 may, in one embodiment, be a forward-and-reverse ratchet system. In the preferred embodiment, the tension control mechanism 40 is comprised of a worm gear 32 driven by a dial handle 51 to turn a drum 35 through enmeshment with a gear chain 33. The drum 35 spools thereon the proximal end 50 of the inner steel wire 37. The dial handle 51 is essentially circular and may have fluting to facilitate a hand grip. When the dial handle 51 is rotated clockwise, the drum 35 spools-in to tighten tension at the hammock 4 and reverses, spooling-out to loosen tension, by counter-clockwise rotation.

Figure 10:
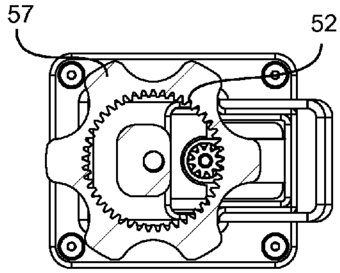
FIG. 10 is a section view taken along lines 10-10 of FIG. 9.
Figure 11:
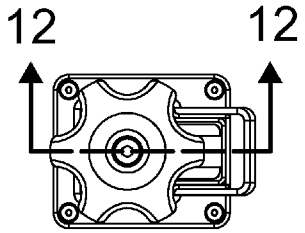
FIG. 11 is a plan view of the traction control mechanism.
Figure 13:
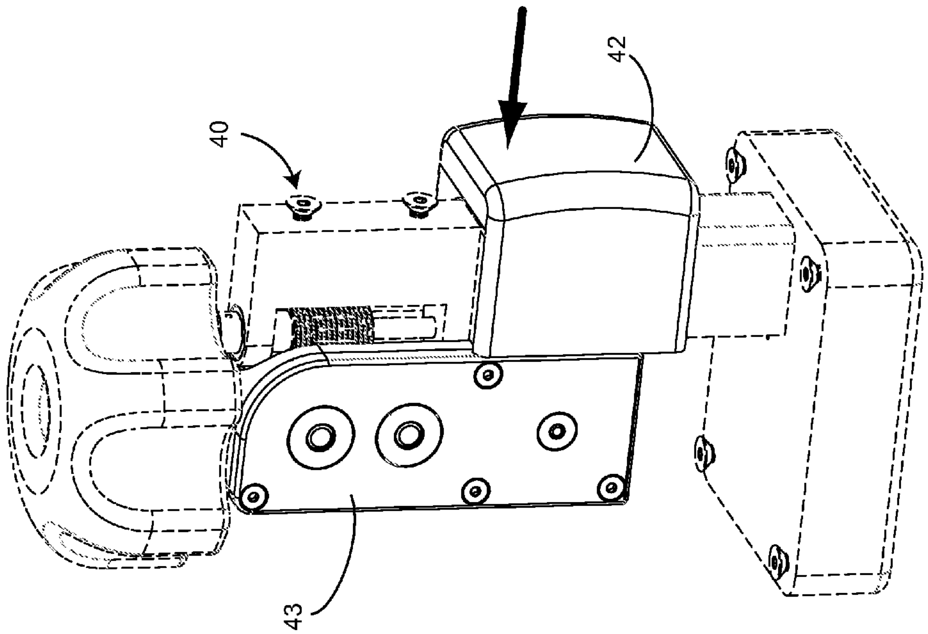
FIG. 13 is a perspective view of the tension control mechanism with the casing removed to show the gear chassis and button in solid line.
Figure 14:
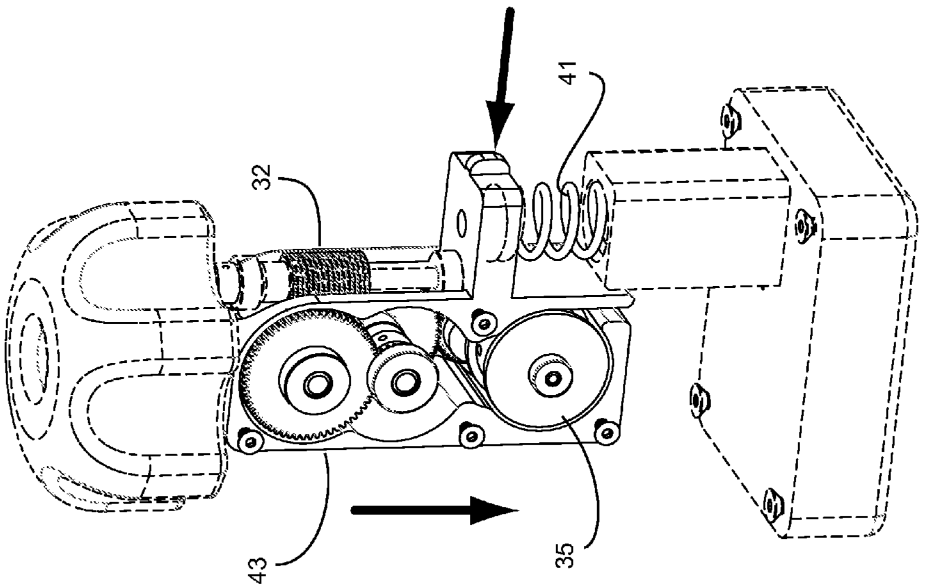
FIG. 14 is the view of FIG. 13 with the gear chassis cover and button removed to show the gear nest and release spring.

In the preferred embodiment, the dial handle 51 has an inside gear 52 which meshes with the worm gear 32 on an offset axis (FIG. 10). The greater the offset, the greater the mechanical leverage applied. The mechanical leverage can be further augmented by a differential enlargement of the dial diameter. The worm gear 32 meshes with a worm gear follower 34 in the gear chain 33 (FIG. 12). A phenomenon of worm gears is that, while the worm gear can easily turn the follower, the follower cannot turn the worm gear. This is because the pitch on the worm is so shallow that, when the follower tries to turn it, the friction between the gears holds the worm in place. As a consequence, rotational positioning can be advanced and held with a worm gear without the interfering geometry common to a ratchet system. The remaining linked gears in the gear chain 33 provide further gear reduction opportunity for driving the drum 35. By manipulating the gear ratios in the design of the gear chain 33, a balance can be struck between power and revolution speed. A gear ratio is, mathematically, the ratio of the number of teeth in a driver/driven gear pair. The gear ratio of a compound gear set, such as that of the gear chain 33, is the multiplication of the ratios of each pairing. Directional correction can be made by inserting an idler gear in the sequencing. The idler gear otherwise has no effect on the ratio. With proper design, the dial will be easy to handle and turn and a full revolution of the drum will amount to only a slight rotation of the dial.

In the preferred embodiment, the gear chain 33 is housed in a gear chassis 43. The gear chassis 43 may be shifted either vertically or horizontally if sufficient excess internal space is provided in the tension control mechanism 40 (see arrows in FIGS. 13 and 14). In either case of displacement of the gear chassis 43, the worm gear follower 34 will disengage the worm gear 32 causing the tension to be released in the Bowden cable 36. A release spring 41 may be used to bias the chassis 43 to its operational engagement. When the compression strength of the release spring 41 is exceeded by the applied tension, the release spring 41 will yield and the gear chassis 43 will automatically disengage by shifting downwardly. The release spring 41 may be further calibrated by means of an adjustment screw 53 (FIG. 12). Alternatively, or additionally, an emergency release mechanism may be provided by a button 42. Button 42 may be pressed by hand, or squeezed by palm action, to drive the gear chassis 43 sideways and break connection with the worm gear 32. If the bending moment of the release spring 41 is not sufficient to hold a horizontal register of the gear chassis 43, the gear chassis 43 may be buffered against a side wall by an elastomeric insert having a slip surface (not shown).

In the preferred embodiment, the tubular members 8 of frame 3 are fabricated from 1.25" steel or aluminum tubing, although PVC tubing of a sufficiently beefy wall construction can be used. The constituents of hingeable joints 13 and T-joints 15 are preferably injection molded from nylon resin. Alternative resins of comparable toughness can be used, such as acrylonitrile butadiene styrene (ABS). The parts can also be machined from aluminum or other metal blanks The hinge pins are preferably steel pins. The fabric web 12 and the hammock 4 may be sewn from canvas, duck or a synthetic woven material, such as polyester. The hammock 4 may be lined with a soft, or napped, material for comfort and abrasion prevention. The occiput collar 5 may be molded from closed-cell foam, such as urethane, and may be attached to the hammock 4 by sewing, by Velcro® hook-and-eye patches, or by other known attachment means. The stabilizer lines 6 may be elasticized "shock cord", or otherwise rubberized surgical tubing, and may be attached by sewn-in, or Velcro'd-on, D-rings. The gears of the gear chain 32, and the bushings suspending them, are preferably stock metal components, but may otherwise be custom-molded from nylon. The gear chassis 43 is preferably fabricated as a machined metal part. The dial handle 51 is preferably molded from nylon, or the equivalent. The remaining components of tension control mechanism 40 may be molded from commodity resins, such as polyethylene (PE), polypropylene (PP) or impact polystyrene (HIPS). The Bowden cable is available in standard gauges and essentially unlimited length from stock supply. The release spring 41 is preferably a coil spring of tempered steel composition.

In operation, the portable decompression device 1 can be unfolded and extended to its envelope space of approximately 26" wide by 40" deep by 27" high. The erect A-frame 25 forms an isosceles triangle with base angles of approximately 66°. During operation, the patient lies comfortably upon the fabric web 12 with the patient's head suspended in the hammock 4. The weight of the patient's body 2 holds the apparatus in place. The tension control mechanism 40 may be handled with the patient's upper arms at rest beside the body 2. By bending from the elbows, one of the patient's hands may hold the control mechanism while the other hand rotates the dial. The amount of tension to be applied and the cyclical frequency of the stretching and relaxing optimal for invoking imbibition, as well as the preferred critical value 31 defining the safe limit of applied tension, may be proscribed in the individual circumstance by a licensed professional. The portable decompression device 1 may be folded and rolled together with the fabric and control components to reduce size to approximately 8" in girth and 28" in length.

It is to be understood that the invention is not limited in its application to the details of construction, to the arrangements of the components and to the method of using set forth in the preceding description or illustrated in the drawings. For example, the first vertical angle 22 could be made adjustable in order to customize the pull direction. In addition, the manual tension control 40 could be replaced with a motorized version. Also, it is to be understood that the phraseology and terminology employed herein are for the purpose of the description and should not be regarded as limiting.

What is claimed is:

1. A portable device for spinal decompression therapy, comprising:

- a support base with two hingeably-attached horizontal members deployed a shoulder-width apart;
- a fabric web stretched between the horizontal members for deployment at least partially beneath the back of a person lying against said fabric web, the body-weighed fabic web anchoring the support base to a level surface;
- a vertical structure hingeably attached to the support base and deployed there upon at a first preferred vertical angle to fixedly position a distal end overhead;
- a hammock suspended from the distal end to cradle the person's head at a second preferred vertical angle;
- a means for incrementally applying and releasing tension to the hammock, alternately stretching and relaxing the person's cervical spine along the second preferred vertical angle, the tension releasing automatically at a preferred critical value;

whereby, the portable device may be folded and rolled up into a compact profile.

2. The portable device of claim 1, wherein the vertical structure is an A-frame with vertical struts hingeably connected at the apex thereof.

3. The portable device of claim 2, wherein all hingeable joints are reversibly locking hingeable joints.

4. The portable device of claim 3, wherein the means for incrementally applying and releasing tension further comprises a gear chain in enmeshment with the worm gear, said gear chain designed to achieve mechanical leverage for comfortable hand operation.

5. The portable device of claim 4, wherein the means for incrementally applying and releasing tension further comprises a drum driven by the gear chain, the drum spooling an inner steel wire of a Bowden cable, said inner steel wire connected at a distal end thereof to the hammock.

6. The portable device of claim 4, wherein the gear chain is biased into engagement with the worm gear by a spring until the preferred critical value is exceeded, where upon the tension applied to the hammock becomes automatically released through disengagement of the worm gear.

7. The portable device of claim 4, wherein the gear chain may be selectively disengaged from the worm gear by pressing a button, the button activation providing an emergency release of the tension applied to the hammock.

8. The portable device of claim 1, wherein the means for incrementally applying and releasing tension comprises a reversing worm gear actuated by rotating a handle, said worm gear locking progress at each advanced position of the handle.

9. The portable device of claim 1, wherein the means for incrementally applying and releasing tension comprises a drum which spools an inner steel wire of a Bowden cable, said inner steel wire connected at a distal end thereof to the hammock.

10. The portable device of claim 1, wherein the means for incrementally applying and releasing tension further comprises a spring mechanism for automatically releasing tension, said spring mechanism characterized by a compression strength equivalent to the preferred critical value.

11. The portable device of claim 1, wherein the hammock is enhanced with an occiput collar to comfortably and tractionably grip the back of the person's head beneath the skull curvature at the neck.

12. The portable device of claim 11, wherein the occiput collar is comprised of an ergonomically-shaped elastomeric material featuring raised fingers for grip enhancement.

13. The portable device of claim 1, wherein the means for incrementally applying and releasing tension can be operated without affecting any muscle of the back.

* * * * *